(12) United States Patent
Hakozaki et al.

(10) Patent No.: US 9,597,271 B2
(45) Date of Patent: Mar. 21, 2017

(54) COSMETIC COMPOSITIONS AND METHODS

(71) Applicant: The Procter & Gamble Company, Cincinnati, OH (US)

(72) Inventors: Tomohiro Hakozaki, Cincinnati, OH (US); Leo Timothy Laughlin, II, Mason, OH (US); Michael Christopher Sabino, Liberty Township, OH (US)

(73) Assignee: The Procter & Gamble Company, Cincinatti, OH (US)

( * ) Notice: Subject to any disclaimer, the term of this patent is extended or adjusted under 35 U.S.C. 154(b) by 82 days.

(21) Appl. No.: 14/521,742

(22) Filed: Oct. 23, 2014

(65) Prior Publication Data

US 2015/0118169 A1     Apr. 30, 2015

Related U.S. Application Data

(60) Provisional application No. 61/895,271, filed on Oct. 24, 2013.

(51) Int. Cl.

| | |
|---|---|
| *A61K 8/00* | (2006.01) |
| *A61K 8/36* | (2006.01) |
| *A61K 8/06* | (2006.01) |
| *A61K 8/67* | (2006.01) |
| *A61Q 19/02* | (2006.01) |
| *A61K 8/37* | (2006.01) |

(52) U.S. Cl.
CPC ............ *A61K 8/361* (2013.01); *A61K 8/06* (2013.01); *A61K 8/37* (2013.01); *A61K 8/675* (2013.01); *A61Q 19/02* (2013.01); *A61K 2800/592* (2013.01)

(58) Field of Classification Search
CPC .......... A61K 8/361; A61K 8/06; A61K 8/675; A61K 8/28; A61K 8/592; A61K 8/34; A61Q 8/37

See application file for complete search history.

(56) References Cited

U.S. PATENT DOCUMENTS

| | | | |
|---|---|---|---|
| 3,755,560 A | 8/1973 | Dickert | |
| 4,421,769 A | 12/1983 | Xon | |
| 5,053,230 A | 10/1991 | Gazzani | |
| 5,262,153 A | 11/1993 | Mishima | |
| 6,224,888 B1* | 5/2001 | Vatter et al. | 424/401 |
| 6,238,678 B1* | 5/2001 | Oblong | A61K 8/42 424/401 |
| 6,555,143 B2 | 4/2003 | Miller | |
| 7,776,915 B2 | 8/2010 | Morariu | |
| 7,803,966 B2 | 9/2010 | Oddos | |
| 2004/0102358 A1 | 5/2004 | Scivoletto | |
| 2004/0248771 A1 | 12/2004 | Raggi | |
| 2006/0088616 A1 | 4/2006 | Stone | |
| 2006/0089277 A1 | 4/2006 | Harding | |
| 2007/0231288 A1 | 10/2007 | Arnaud | |
| 2008/0152682 A1* | 6/2008 | Simoulidis | A61K 8/23 424/401 |
| 2008/0193396 A1* | 8/2008 | Spina | A61K 8/361 424/59 |
| 2008/0312169 A1 | 12/2008 | Johnson | |
| 2009/0317341 A1 | 12/2009 | Madison | |
| 2010/0249244 A1* | 9/2010 | Fuller | A61K 9/0014 514/701 |
| 2011/0033404 A1 | 2/2011 | Madison | |
| 2012/0121534 A1 | 5/2012 | Thorel | |

FOREIGN PATENT DOCUMENTS

| | | |
|---|---|---|
| CN | 103637952 | 3/2014 |
| EP | 107885 | 5/1984 |
| EP | 1 200 055 B1 | 5/2002 |
| FR | 2864445 | 4/2006 |
| FR | 2877222 | 10/2008 |
| FR | 2988292 | 3/2014 |
| GB | 2472379 | 2/2011 |
| JP | 2000086442 | 3/2000 |
| RU | 2013088 | 5/1994 |
| WO | WO9846206 | 10/1998 |
| WO | WO 00/47182 A1 | 8/2000 |
| WO | WO 2006/117055 A1 | 11/2006 |
| WO | WO201224399 | 2/2012 |

OTHER PUBLICATIONS

Mintel GNPD Oct. 1, 2012 (Oct. 1, 2012), Procter & Gamble: "Pro-X by Olay Professional White", Database accession No. 1920800.
Mintel Database GNPD Mar. 1, 2013 (Mar. 1, 2013), Too Cool for School: "McGirly Rice Wine Secret Whitening 36.5 Degree C Eye Gel Mask", Database accession No. 2016995.
Mintel Database GNPD Jul. 1, 2013 (Jul. 1, 2013), Physicians Formula: "Plump Potion Volume Lipgloss", Database accession No. 2117239.
Mintel Database GNPD Nov. 1, 2011 Xianweina Cosmetics: "Sivia Olive Essence Eye Cream", Database accession No. 1669066.
Mintel Database GNPD; Sep. 1, 2013 Demain Nature: "DN UNIK Whitening Night Cream", Database accession No. 2200359.
Hakozaki. T., et al."A regulator of ubiquitin—proteasome activity,2-hexyldecanol, suppresses melanin synthesis and the appearance of facial hyperpigmented spots" British Journal of Dermatology 2013, 169 (Supp 2), pp. 39-44.
Watabe el al., "Regulation of tyrosinase processing and trafficking by organellar pH and by proteasome activity", J Biol Chem 2004, 279, pp. 7971-7981.
International Search Report PCT/US2014/061856; Mailing Date Feb. 6, 2015.
Ando et al., "Role of the ubiquitin—proteasome system in regulating skin pigmentation", Int J Mol Sci 2009, 10, pp. 4428-4434.
Anti-Ageing Face Sunscreen SPF 30, Record ID: 2362420, Mary Cohr, May 2014 http://www.gnpd.com/.

(Continued)

*Primary Examiner* — Nannette Holloman
(74) *Attorney, Agent, or Firm* — John G. Powell

(57) ABSTRACT

A cosmetic composition for topical application to skin is provided. The cosmetic composition includes vitamin B3 compound, a ricinoleate compound and a dermatologically acceptable carrier. The vitamin B3 compound and the ricinoleate beneficially or even synergistically up-regulate proteasomal protease activity as evidenced by a higher observed net luminescence value relative to the calculated net luminescence value in B16 melanoma cells.

9 Claims, 1 Drawing Sheet

(56) References Cited

OTHER PUBLICATIONS

Anti-Ageing Eye Contour Sunscreen SPF 30, Record ID: 2362281, Mary Cohr, May 2014 http://www.gnpd.com/.
Vitamin C Brightening Serum, Record ID: 1986638, Guinot, Jan. 2013 http://www.gnpd.com/.
Enriched New Youth Body Care, Record ID: 1874046, Mary Cohr, Aug. 2012 http://www.gnpd.com/.
14 Days Serum, Record ID: 1874068, Mary Cohr, Aug. 2012 http://www.gnpd.com/.
Age Serum Eyes, Record ID: 1787048, Guinot, Apr. 2012 http://www.gnpd.com/.
E.V.E. Essential Vital Elements Serum Source, Record ID: 1765733, Institut Esthederm, Mar. 2012 http://www.gnpd.com/.
Serum, Record ID: 1670831, Mary Cohr, Nov. 2011 http://www.gnpd.com/.
Restorative Facial Wash, Record ID: 1458635, S&J International Enterprises, Dec. 2010 http://www.gnpd.com/.
Biovitalising Matrix Cream, Record ID: 1247930, Bioderma, Feb. 2010 http://www.gnpd.com/.
Lifting Matrix Cream, Record ID: 1250986, Bioderma, Jan. 2010 http://www.gnpd.com/.
Matricium, Record ID: 1251311, COC farmaceutici, Jan. 2010.
Intensive Regeneration Matrix Concentrate, Record ID: 1270126, Bioderma Jan. 2010 http://www.gnpd.com/.

\* cited by examiner

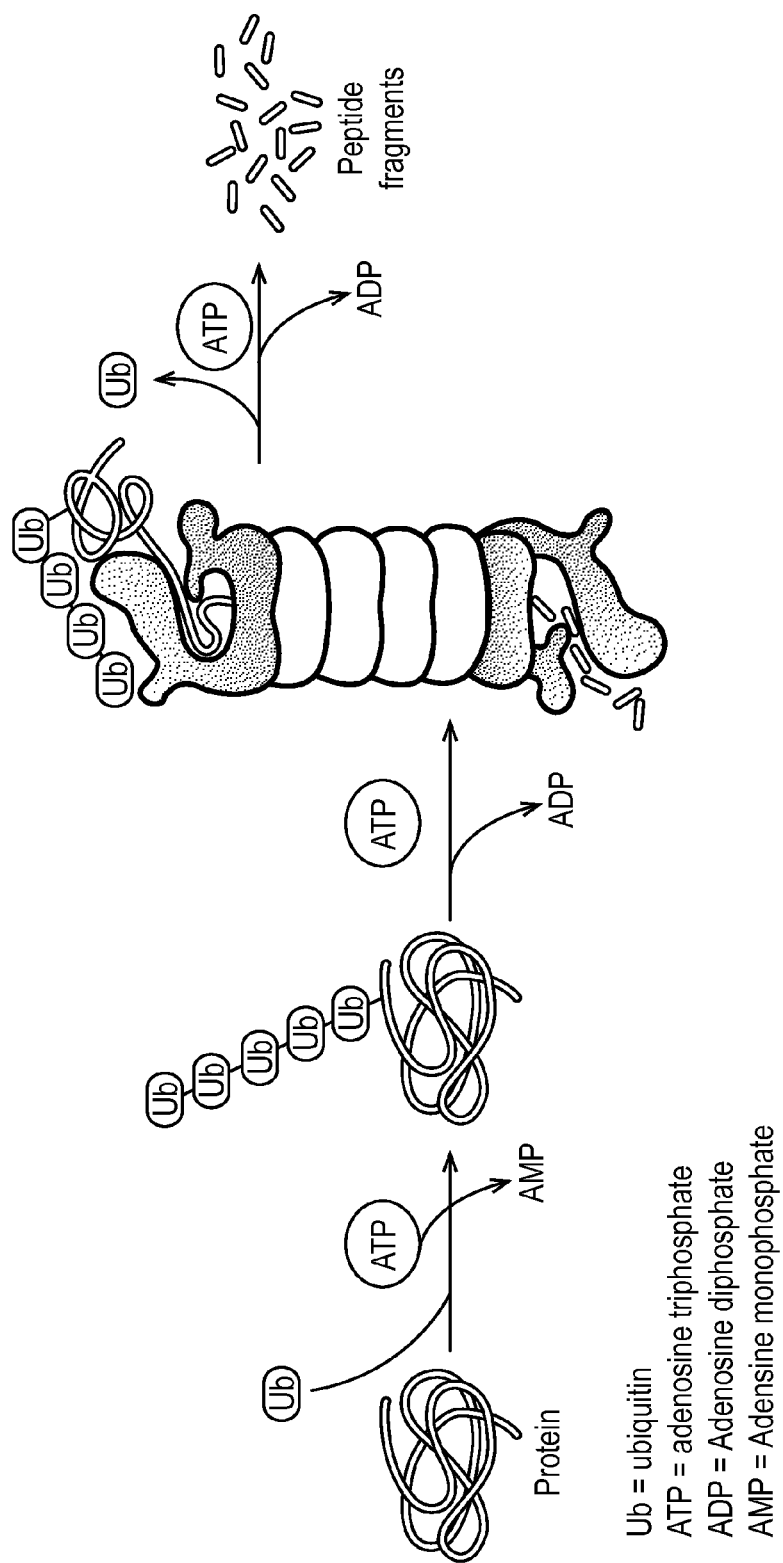

COSMETIC COMPOSITIONS AND METHODS

FIELD

The present disclosure is directed to cosmetic compositions and methods for up-regulating proteasomal protease activity.

BACKGROUND

Skin tone evenness and/or the appearance of hyperpigmentary spots, such as solar lentigines (age spots), are common concerns among beauty conscious consumers. As such, cosmetic compositions and methods for addressing these consumer concerns are continuing areas of high interest. In melanocytes, the ubiquitin-proteasome system is known to regulate skin pigmentation by degrading tyrosinase or microphthalmia-associated transcription factor. Further, it is believed that up-regulation of proteasomal protease activity may lead to reduced melanin production in melanocytes. See, e.g., Hakozaki et al., A regulator of ubiquitin-proteasome activity, 2-hexyldecanol, suppresses melanin synthesis and the appearance of facial hyperpigmented spots, British Journal of Dermatology 2013, 169 (Supp 2), pp 39-44. See, also, Watabe et al., Regulation of tyrosinase processing and trafficking by organellar pH and by proteasome activity, J Biol Chem 2004, 279, pp 7971-81 and Ando et al., Role of the ubiquitin-proteasome system in regulating skin pigmentation, Int J Mol Sci 2009, 10, pp 4428-34. Improved cosmetic compositions and methods that may up-regulate proteasomal protease activity are believed to be desirable.

SUMMARY

In one aspect, a cosmetic composition for topical application to skin is provided. In one aspect, the cosmetic composition includes a vitamin B3 compound, a ricinoleate compound and a dermatologically acceptable carrier.

In another aspect, the cosmetic composition comprises niacinamide or a derivative thereof having a concentration from about 0.5% to about 10% by weight of the cosmetic composition. The cosmetic composition also includes a ricinoleate compound having a concentration from about 0.05% to about 10% by weight of the cosmetic composition. The cosmetic composition also includes a dermatologically acceptable carrier. The ratio of the concentration of niacinamide compound to ricinoleate compound is from about 150:1 to about 1:2.

In still another aspect, a method of treating a facial skin surface is provided. The method comprises identifying a target facial skin surface where skin lightening is desired; and applying a cosmetic composition to the target facial skin surface, wherein the cosmetic composition comprises a vitamin $B_3$ compound, a ricinoleate compound and a dermatologically acceptable carrier.

BRIEF DESCRIPTION OF THE DRAWINGS

It is believed that the disclosure will be better understood from the following description taken in conjunction with the accompanying drawings. The referenced drawings are not to be construed as limiting the scope of the present invention.

FIG. 1 is a schematic illustration of a proteasomal protease pathway.

DETAILED DESCRIPTION

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

"Cosmetic" means providing a desired visual effect on an area of the human body. The visual cosmetic effect may be temporary, semi-permanent, or permanent. Some non-limiting examples of "cosmetic products" include products that leave color on the face, such as foundation, mascara, concealers, eye liners, brow colors, eye shadows, blushers, lip sticks, lip balms, face powders, solid emulsion compact, and the like.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications. In some embodiments, cosmetic agents may be incorporated in a cosmetic composition comprising a dermatologically acceptable carrier suitable for topical application to skin. Cosmetic agents include, but are not limited to, (i) chemicals, compounds, small or large molecules, extracts, formulations, or combinations thereof that are known to induce or cause at least one effect (positive or negative) on skin tissue; (ii) chemicals, compounds, small molecules, extracts, formulations, or combinations thereof that are known to induce or cause at least one effect (positive or negative) on skin tissue and are discovered, using the provided methods and systems, to induce or cause at least one previously unknown effect (positive or negative) on the skin tissue; and (iii) chemicals, compounds, small molecules, extracts, formulations, or combinations thereof that are not known have an effect on skin tissue and are discovered, using the provided methods and systems, to induce or cause an effect on skin tissue.

Some examples of cosmetic agents or cosmetically actionable materials can be found in: the PubChem database associated with the National Institutes of Health, USA (http://pubchem.ncbi.nlm.nih.gov); the Ingredient Database of the Personal Care Products Council (http://online.personalcarecouncil.org/jsp/Homejsp); and the 2010 International Cosmetic Ingredient Dictionary and Handbook, 13$^{th}$ Edition, published by The Personal Care Products Council; the EU Cosmetic Ingredients and Substances list; the Japan Cosmetic Ingredients List; the Personal Care Products Council, the SkinDeep database (URL: http://www.cosmeticsdatabase.com); the FDA Approved Excipients List; the FDA OTC List; the Japan Quasi Drug List; the US FDA Everything Added to Food database; EU Food Additive list; Japan Existing Food Additives, Flavor GRAS list; US FDA Select Committee on GRAS Substances; US Household Products Database; the Global New Products Database (GNPD) Personal Care, Health Care, Food/Drink/Pet and Household database (URL: http://www.gnpd.com); and from suppliers of cosmetic ingredients and botanicals.

Other non-limiting examples of cosmetic agents include botanicals (which may be derived from one or more of a root, stem bark, leaf, seed or fruit of a plant). Some botanicals may be extracted from a plant biomass (e.g., root, stem, bark, leaf, etc.) using one more solvents. Botanicals may comprise a complex mixture of compounds and lack a distinct active ingredient. Another category of cosmetic agents are vitamin compounds and derivatives and combinations thereof, such as a vitamin B3 compound, a vitamin B5 compound, a vitamin B6 compound, a vitamin B9 compound, a vitamin A compound, a vitamin C compound, a vitamin E compound, and derivatives and combinations thereof (e.g., retinol, retinyl esters, niacinamide, folic acid, panthenol, ascorbic acid, tocopherol, and tocopherol acetate). Other non-limiting examples of cosmetic agents include sugar amines, phytosterols, hexamidine, hydroxy acids, ceramides, amino acids, peptides, and polyols.

"Cosmetic composition" means any composition comprising a cosmetic agent that is suitable for topical application on mammalian skin.

"Derivative" means any compound derived from a given compound, including but not limited to amide, ether, ester, amino, carboxyl, acetyl, alcohol derivatives and/or salts of a given compound.

"Dermatologically acceptable" means that a composition or components described are suitable for use in contact with human skin tissue.

"Effective amount" means an amount of a compound or composition sufficient to significantly induce a positive appearance and/or feel benefit.

"Facial skin surface" means one or more of forehead, periorbital, cheek, perioral, chin, and nose skin surfaces.

I. Cosmetic Compositions

Various cosmetic compositions and, more specifically, cosmetic compositions for application to a skin surface, are provided. The cosmetic compositions comprise a combination of a vitamin B$_3$ compound and a ricinoleate compound. The cosmetic compositions may be provided in various product forms that include, but are not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. The cosmetic composition form may follow from the particular dermatologically acceptable carrier chosen, if present in the composition.

A. Vitamin B$_3$ Compounds

The cosmetic composition comprises a vitamin B$_3$ compound. As used herein, "vitamin B$_3$ compound" means a compound having the formula:

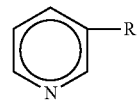

wherein R is —CONH$_2$ (i.e., niacinamide), —COOH (i.e., nicotinic acid) or —CH$_2$OH (i.e., nicotinyl alcohol); and derivatives of the foregoing. Exemplary derivatives of the foregoing vitamin B3 compounds may include nicotinic acid esters, including non-vasodilating esters of nicotinic acid, nicotinyl amino acids, nicotinyl alcohol esters of carboxylic acids, nicotinic acid N-oxide and niacinamide N-oxide. Other derivatives of the vitamin B3 compound are derivatives of niacinamide resulting from substitution of one or more of the amide group hydrogens. Some non-limiting examples of derivatives of niacinamide useful herein include nicotinyl amino acids, derived, for example, from the reaction of an activated nicotinic acid compound (e.g., nicotinic acid azide or nicotinyl chloride) with an amino acid, and nicotinyl alcohol esters of organic carboxylic acids (e.g., C1-C18). Specific examples of such derivatives include nicotinuric acid (C8 H8 N2 O3) and nicotinyl hydroxamic acid (C6 H6 N2 O2). One example of a niacinamide derivative that may be suitable for use is nicotinamide ribose. Exemplary nicotinyl alcohol esters include nicotinyl alcohol esters of the carboxylic acids salicylic acid, acetic acid, glycolic acid, palmitic acid and the like.

More preferably, the cosmetic composition comprises niacinamide (sometimes also referred to as nicotinamide or nicotinic acid amide) or a derivative thereof. Niacinamide is available from a number of sources, e.g., the Sigma Chemical Company (St. Louis, Mo.,); ICN Biomedicals, Inc. (Irvin, Calif.) and Aldrich Chemical Company (Milwaukee, Wis.).

Suitable derivatives may include any derivative having substantially the same or greater activity in the proteasomal protease assay described herein when combined with one or more ricinoleate compounds, preferably when combined with one or more of ricinoleic acid, ethyl ricinoleate, methyl ricinoleate, potassium ricinoleate, sodium ricinoleate, zinc ricinoleate, acetyl ricinoleic acid, glyceryl ricinoleate or glyceryl acetyl ricinoleate. In some preferred embodiments, "substantially the same" means that the net observed luminescence count of the combination of a ricinoleate compound and the derivative in a dimethyl sulfoxide (sometimes referred to as DMSO) vehicle is within ±10% of the net calculated luminescence count. In some preferred embodiments, "greater activity" means that the net observed luminescence count of the combination of a ricinoleate compound and the derivative in a DMSO vehicle is more than 1,3, 1.4, 1.5 1.6, or 1.7 (and/or less than 2) tines greater than the net calculated luminescence count. Alternatively, the difference between the net observed luminescence count and the net calculated luminescence count is greater than about 700, 800, 900, 1000, 1100, 1200, 1300, 1400 and/or less than 20,000, 15,000, 10,000, 5,000, 2,500 or 2,000.

The vitamin $B_3$ compound may have a concentration from about 0.05%, 0.5%, 1%, 2%, 3%, 4% or 5% to about 15%, 10%, 8% or 6% by weight of the cosmetic composition.

B. Ricinoleate Compounds

The cosmetic composition further comprises a ricinoleate compound. As used herein, "ricinoleate compound" means ricinoleic acid and derivatives thereof. Some examples of ricinoleate compounds include acetylated lanolin ricinoleate, acetyl glyceryl ricinoleate, butyl acetyl ricinoleate, cetyl acetyl ricinoleate, cetyl ricinoleate, cetyl ricinoleate benzoate, ethylhexyl polyricinoleate, ethyl ricinoleate, glyceryl diricinoleate, glyceryl diricinoleate/IPDI copolymer, glyceryl ricinoleate, glyceryl ricinoleate SE, glyceryl triacetyl ricinoleate, glycol ricinoleate, isopropyl ricinoleate, lanolin ricinoleate, methyl acetyl ricinoleate, methyl ricinoleate, octyldodecyl ricinoleate, PEG-20 diricinoleate, PEG-8 di/triricinoleate, PEG-15 glyceryl ricinoleate, PEG-20 glyceryl ricinoleate, PEG/PPG-10/2 diricinoleate, PEG/PPG-32/3 diricinoleate, PEG/PPG-10/2 ricinoleate, PEG/PPG-32/3 ricinoleate, PEG-2 ricinoleate, PEG-7 ricinoleate, PEG-8 ricinoleate, PEG-9 ricinoleate, phytosteryl ricinoleate, polyglyceryl-8 decaerucate/decaisostearate/decaricinoleate, polyglyceryl-3 pentaricinoleate, polyglyceryl-6 pentaricinoleate, polyglyceryl-10 pentaricinoleate, polyglyceryl-3 polyricinoleate, polyglyceryl-4 polyricinoleate, polyglyceryl-5 polyricinoleate, polyglyceryl-6 polyricinoleate, polyglyceryl-10 polyricinoleate, polyglyceryl-3 ricinoleate, polyglyceryl-6 ricinoleate, polylactate/ricinoleate, polyoxypropylene sorbitol ricinoleate, potassium ricinoleate, propylene glycol diricinoleate, propylene glycol ricinoleate, sodium ricinoleate, sucrose ricinoleate, sulfurized TEA-ricinoleate, TEA-diricinoleate, TEA-diricinoleate, tetrahydrofurfuryl ricinoleate and zinc ricinoleate. Some preferred examples of ricinoleate compounds include, but are not limited to, ricinoleic acid, ethyl ricinoleate, methyl ricinoleate, potassium ricinoleate, sodium ricinoleate, zinc ricinoleate, acetyl ricinoleic acid, glyceryl ricinoleate, glyceryl acetyl ricinoleate.

Suitable derivatives may include any derivative having substantially the same or greater activity in the proteasomal protease assay described herein when combined with one or more vitamin $B_3$ compounds, preferably when combined with one or more of niacinamide, nicotinic acid, methyl niconate or nicotinamide ribose. In some preferred embodiments, "substantially the same" means that the net observed luminescence count of the combination of a vitamin $B_3$ compound and the derivative in a DMSO vehicle is within ±10% of the net calculated luminescence count. In some preferred embodiments, "greater activity" means that the net observed luminescence count of the combination of a vitamin B3 compound and the derivative in a DMSO vehicle is more than 1.3, 1.4, 1.5 1.6, or 1.7 (and/or less than 2) times greater than the net calculated luminescence count or, alternatively, difference between the net observed luminescence count and the net calculated luminescence count is greater than about 700, 800, 900, 1000, 1100, 1200, 1300, 1400 and/or less than 20,000, 15,000, 10,000, 5,000, 2,500 or 2,000.

The ricinoleate compound may have a concentration from about 0.01%, 0.025%, 0.05%, 0.5%, 1%, 2%, 3%, 4% or 5% to about 10%, 8% or 6% by weight of the cosmetic composition. The ratio of the concentration of the vitamin $B_3$ compound to the ricinoleate compound concentration may be from about 150:1, 100:1, 80:1, 60:1, 40:1, 20:1 or 15:1 to about 10:1, 9:1, 8:1, 7:1, 6:1, 5:1, 4:1, 3:1, 2:1, 1:1 or 1:2.

C. Combinations of a Vitamin $B_3$ Compound and a Ricinoleate Compound

It is believed that combinations of a vitamin $B_3$ compound and a ricinoleate compound may beneficially up-regulate, even synergistically up-regulate, proteasomal protease activity which may in turn reduce melanin production. FIG. 1 illustrates a proteasomal protease activity pathway. The ubiquitin-proteasome system functions in disposal of many proteins. Ubiquitin is a relatively small polypeptide (about 8000 Daltons) that is activated and attached by E enzymes (E1, E2, E3) to specific proteins that are destined for degradation. The ubiquinated proteins are then recognized by the proteasome complex and processed by proteolytic digestion. Keratinocyte proteins that are subject to regulation by the ubiquitin-proteasome pathway include the vitamin D receptor and the retinoic acid receptor. In melanocytes, the ubiquitin-proteasome system has been shown to regulate skin pigmentation by degrading tyrosinase. This mode of regulating melanogenesis is influenced by phospholipase D and certain fatty acids.

The following proteasomal protease in vitro assay was employed for evaluating activity associated with this pathway. Cultures of B16 melanoma cells (about 25% confluence) were treated with a culture media (Dulbecco's Modified Eagle Medium, 11995-065 Life technologies supplemented with 5% Fetal Bovine Serum, 30-2020, American Tissue Culture Collection and 1% Penicillin/streptomycin, 15140, Life Technologies) and one of 1) a vehicle (DMSO) containing niacinamide, 2) a vehicle (DMSO) containing one of glycerol ricinoleate, sodium ricinoleate and butyl acetyl ricinoleate at varying dilutions, 3) a vehicle (DMSO) containing a combination of niacinamide and one of the ricinoleate compounds listed above, and 4) a vehicle (DMSO) containing 2-hexyl-decanol as a positive control. The final dilution of DMSO in the culture medium was 1% in all instances. The treated melanoma cells were incubated in multi-well plates at 37° C. in a $CO_2$ incubator for a period of 20 to 24 hours. The treated cells were thereafter lyzed by removing the culture medium and replacing it with 100 uL/well of CellGlo lysis reagent (available from Promega, Wis., USA) followed by incubation at room temperature for about 10 minutes. A luminogenic substrate containing a Suc-LLVY peptide sequence recognized by the 20S proteasome was added to the B16 cultures, and the mixtures were incubated in multi-well plates at a temperature of 25° C. for approximately 10 minutes. Luminescence counts (a unit less measurement from the plate reader) from developing the cleaved substrate with luciferase detection system (ProteasomeGlo® from Promega, Madison, Wis.) was measured in an Envision Plate Reader (Perkin Elmer, Waltham, Mass.). Other plate luminometer/luminescence readers may also be used as known in the art.

Table 1 lists luminescence fold changes values (relative to an untreated control, N=3 for each experiment) and the average value for glyceryl ricinoleate, sodium ricinoleate, butyl acetyl ricinoleate and 2-hexyl decanol in the vehicle using the above described assay. The ricinoleate compounds had similar fold change values to that of 2-hexyldecanol, indicating that the tested ricinoleate compounds apparently have a similar mode of action as 2-hexyldecanol on proteasomal protease activity.

TABLE 1

| | Fold Change Over Control | | | |
|---|---|---|---|---|
| | Glyceryl ricinoleate | Sodium ricinoleate | Butyl acetyl ricinoleate | 2-hexyldecanol |
| #1 | 1.15 | 1.26 | 1.32 | 1.15 |
| #2 | 1.18 | 1.21 | 1.26 | 1.17 |
| Avg. | 1.17 | 1.24 | 1.29 | 1.16 |

Luminescence counts for treatment groups were divided by the luminescence counts from the vehicle control (1% DMSO, as diluted in the culture medium). The results indicate that ricinoleate compounds activate a protease activity consistent with the proteasomal 20S chymotryptic activity. 2-hexyldecanol, a known skin tone agent, was also previously found to activate this proteasomal chymotryptic protease activity. See, e.g., Hakozaki et al., A regulator of ubiquitin-proteasome activity, 2-hexyldecanol, suppresses melanin synthesis and the appearance of facial hyperpigmented spots, British Journal of Dermatology 2013, 169 (Supp 2), pp 39-44.

Table 2 shows the net luminescence counts produced from treating B16 cells with various ricinoleate compounds (0.008 w/v % to 0.000064 w/v %), 250 µM niacinamide and combinations thereof. The data in Table 2 suggests that niacinamide has a lower level of activation of proteasomal chymotryptic activity than the ricinoleate compounds, which activate more substantially. Surprisingly, when combined together, the ricinoleate compounds and niacinamide activate the proteasomal chymotryptic activity to a much level higher (see e.g., observed counts) than the sum of each treatment alone (see, e.g., calculated counts). This synergy is statistically significant at ricinoleate concentrations of 0.0016% and above for glyceryl ricinoleate and, sodium ricinoleate, 0.00032% for butyl acetyl ricinoleate, and 0.008 for methyl ricinoleate. Each data point is the average of 3 replicates.

TABLE 2

Net Luminescence (i.e., treatment luminescence counts − vehicle control luminescence counts)

| w/v % | Glyceryl ricinoleate (GR) | Niacinamide (250 uM) | Niacinamide + GR (observed) | Niacinamide + GR (calculated) | Observed minus calculated | p-value observed vs calculated |
|---|---|---|---|---|---|---|
| 0.008 | 867 | 158 | 1936 | 1025 | 910 | 0.012 |
| 0.0016 | 839 | 158 | 1762 | 997 | 764 | 0.018 |
| 0.00032 | 534 | 158 | 765 | 692 | 72 | 0.34 |
| 0.000064 | 123 | 158 | 298 | 281 | 17 | 0.86 |

| w/v % | Sodium ricinoleate (SR) | Niacinamide (250 uM) | Niacinamide + SR (observed) | Niacinamide + SR (calculated) | Observed minus calculated | p-value observed vs calculated |
|---|---|---|---|---|---|---|
| 0.008 | 2164 | 257 | 3435 | 2421 | 1013 | 0.032 |
| 0.0016 | 1805 | 257 | 2972 | 2062 | 910 | 0.056 |
| 0.00032 | 878 | 257 | 1234 | 1135 | 99 | 0.78 |
| 0.000064 | 123 | 257 | 357 | 380 | −22 | 0.89 |

| w/v % | Butyl acetyl ricinoleate (BAR) | Niacinamide (250 uM) | Niacinamide + BAR (observed) | Niacinamide + BAR (calculated) | Observed minus calculated | p-value observed vs calculated |
|---|---|---|---|---|---|---|
| 0.008 | 2439 | 257 | 3958 | 2696 | 1262 | 0.034 |
| 0.0016 | 2357 | 257 | 4124 | 2614 | 1509 | 0.028 |
| 0.00032 | 2164 | 257 | 4087 | 2421 | 1666 | 0.033 |
| 0.000064 | 1224 | 257 | 1678 | 1481 | 197 | 0.73 |

| w/v % | Methyl ricinoleate (MR) | Niacinamide (250 uM) | Niacinamide + MR (observed) | Niacinamide + MR (calculated) | Observed minus calculated | p-value observed vs calculated |
|---|---|---|---|---|---|---|
| 0.008 | 4222 | 1503 | 12825 | 5724 | 7101 | 0.048 |

Table 3 lists net luminescence counts for glyceryl ricinoleate, some other vitamin B3 compounds (namely nicotinic acid, methyl niconate and 3-pyridinemethanol) and combinations thereof. While none of these vitamin B3 compounds in combination with glyceryl ricinoleate demonstrated an up-regulation that was substantially greater than the sum of the individual net luminescence counts, in contrast to the observed counts of Table 2, the combination of compounds in Table 3 still appears to beneficially up-regulate proteasomal chymotryptic activity in a somewhat additive manner (i.e., the observed luminescence counts for a combination is greater than either of the individual luminescence counts).

D. Dermatologically Acceptable Carriers

The cosmetic compositions may also comprise a dermatologically acceptable carrier (which may also be referred to as a "carrier") within which the vitamin $B_3$ compound and the ricinoleate compound are incorporated to enable the compounds and optional other ingredients to be delivered to the skin. The carrier may contain one or more dermatologically acceptable solid, semi-solid or liquid fillers, diluents, solvents, extenders components, materials and the like. The carrier may be solid, semi-solid or liquid. The carrier may be provided in a wide variety of forms. Some non-limiting

TABLE 3

Net Luminescence (i.e., treatment luminescence counts − vehicle control luminescence counts)

| w/v % | Nicotinic acid (NA) (250 uM) | GR | NA + GR (observed) | NA + GR (calculated) | Observed minus calculated | p-value observed vs calculated |
|---|---|---|---|---|---|---|
| 0.008 | 303 | 789 | 1067 | 1092 | −25 | NA |
| 0.0016 | 303 | 745 | 1056 | 1048 | 8 | 0.68 |
| 0.00032 | 303 | 287 | 556 | 590 | −34 | NA |
| 0.000064 | 303 | 69 | 383 | 372 | 9 | 0.49 |

| w/v % | Methyl niconate (NM) (250 uM) | GR | NM + GR (observed) | NM + GR (calculated) | Observed minus calculated | p-value observed vs calculated |
|---|---|---|---|---|---|---|
| 0.008 | 162 | 789 | 877 | 951 | −74 | NA |
| 0.0016 | 162 | 745 | 743 | 907 | −164 | NA |
| 0.00032 | 162 | 287 | 329 | 449 | −120 | NA |
| 0.000064 | 162 | 69 | 167 | 231 | −64 | NA |

| w/v % | 3-pyridinemethanol (PM) (250 uM) | GR | PM + GR (observed) | Niacinamide + PM (calculated) | Observed minus calculated | p-value observed vs calculated |
|---|---|---|---|---|---|---|
| 0.008 | 105 | 789 | 828 | 894 | −66 | NA |
| 0.0016 | 105 | 745 | 776 | 850 | −74 | NA |
| 0.00032 | 105 | 287 | 373 | 392 | −19 | NA |
| 0.000064 | 105 | 69 | 182 | 174 | 8 | 0.44 |

Table 4 lists net luminescence counts for glyceryl ricinoleate, nicotinamide ribose and combinations thereof. While the combination of nicotinamide ribose and glyceryl rincinoleate did not demonstrate an up-regulation that was substantially greater than the sum of the individual net luminescence counts, in contrast to the observed counts of Table 2, the combination of compounds in Table 4 still appears to beneficially up-regulate proteasomal chymotryptic activity in a somewhat additive manner (i.e., the observed luminescence counts for a combination is greater than either of the individual luminescence counts).

examples include simple solutions, (aqueous or oil based), emulsions, and solid forms (e.g., gels, sticks, flowable solids, amorphous materials).

The carriers may contain one or more dermatologically acceptable, hydrophilic diluents. As used herein, "diluent" includes materials in which the vitamin $B_3$ compound and/or ricinoleate compound can be dispersed, dissolved, or otherwise incorporated. Hydrophilic diluents include water, organic hydrophilic diluents such as lower monovalent alcohols (e.g., C1-C4) and low molecular weight glycols and polyols, including propylene glycol, polyethylene glycol

TABLE 4

Net Luminescence (i.e., treatment luminescence counts − vehicle control luminescence counts)

| w/v % | Nicotinamide Ribose (NB) (250 uM) | GR | NB + GR (observed) | NB + GR (calculated) | Observed minus calculated | p-value observed vs calculated |
|---|---|---|---|---|---|---|
| 0.008 | 392 | 1125 | 1583 | 1517 | 66 | .74 |
| 0.0016 | 392 | 1258 | 1463 | 1650 | −187 | NA |
| 0.00032 | 392 | 518 | 977 | 910 | 67 | .54 |
| 0.000064 | 392 | 191 | 563 | 583 | −20 | NA |

(e.g., Molecular Weight 200-600 g/mole), polypropylene glycol (e.g., Molecular Weight 425-2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Carriers may also be in the form of an emulsion, such as oil-in-water emulsions, water-in-oil emulsions, and water-in-silicone emulsions. An emulsion may generally be classified as having a continuous aqueous phase (e.g., oil-in-water and water-in-oil-in-water) or a continuous oil phase (e.g., water-in-oil and oil-in-water-in-oil). The oil phase may comprise silicone oils, non-silicone oils such as hydrocarbon oils, esters, ethers, and the like, and mixtures thereof. The aqueous phase may comprise water, such as a solution as described above. However, in other embodiments, the aqueous phase may comprise components other than water, including but not limited to water-soluble moisturizing agents, conditioning agents, anti-microbials, humectants and/or other water-soluble skin care actives. In one embodiment, the non-water component of the composition comprises a humectant such as glycerin and/or other polyols. Emulsions may also contain from about 1% to about 10% or from about 2% to about 5%, of an emulsifier, based on the weight of the carrier. Emulsifiers may be nonionic, anionic or cationic. Some suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon el al.; and McCutcheon's Detergents and Emulsifiers, North American Edition, pages 317-32 (1986), each incorporated herein by reference.

E. Optional Components

A wide variety of optional components/ingredients may be included in the cosmetic compositions. For example, the cosmetic compositions may include absorbents, abrasives, anticaking agents, antifoaming agents, antimicrobial agents, binders, biological additives, buffering agents, bulking agents, chemical additives, cosmetic biocides, denaturants, cosmetic astringents, drug astringents, external analgesics, film formers, humectants, opacifying agents, fragrances, pigments, colorings, essential oils, skin sensates, emollients, skin soothing agents, skin healing agents, pH adjusters, plasticizers, preservatives, preservative enhancers, propellants, reducing agents, additional skin-conditioning agents, skin penetration enhancing agents, skin protectants, solvents, suspending agents, emulsifiers, thickening agents, solubilizing agents, sunscreens, sunblocks, ultraviolet light absorbers or scattering agents, sunless tanning agents, anti-oxidants and/or radical scavengers, chelating agents, sequestrants, anti-acne agents, anti-inflammatory agents, anti-androgens, depilation agents, desquamation agents/exfoliants, organic hydroxy acids, vitamins and derivatives thereof, and natural extracts. Such other materials are known in the art. Nonexclusive examples of such materials are described in Harry's Cosmedcology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker, Inc.; in The Chemistry and Manufacture of Cosmetics, 2nd. ad., deNavarre (Van Nostrand 1962-1965); and in The Handbook of Cosmetic Science and Technology, 1st Ed. Knowlton & Pearce (Elsevier 1993).

II. Methods of Cosmetic Treatment

Various cosmetic treatments may be employed. Skin surfaces of the most concern tend to be those not typically covered by clothing such as facial skin surfaces, hand and arm skin surfaces, foot and leg skin surfaces, and neck and chest skin surfaces. In particular, facial skin surfaces, including the forehead, perioral, chin, periorbital, nose, and/or cheek skin surfaces, may be treated with the cosmetic compositions described herein.

The treatment method may include applying the cosmetic composition to a previously identified area of skin in need of treatment, or an area where one seeks to prevent, treat or reduce the appearance of age spots and/or improve skin tone evenness. Many regimens exist for the application of the cosmetic composition. The cosmetic composition may be applied at least once a day, twice a day, or on a more frequent daily basis, during a treatment period. When applied twice daily, the first and second applications are separated by at least 1 to 12 hours. Typically, the cosmetic composition may be applied in the morning and/or in the evening before bed.

The treatment period is ideally of sufficient time to provide an improvement in the appearance of the age spots or skin tone evenness. The treatment period may be at least 1 week, and in some embodiments the treatment period may last about 4 weeks, 8 weeks, or 12 weeks. In certain embodiments, the treatment period will extend over multiple months (i.e., 3-12 months) or multiple years. In one embodiment the cosmetic composition is applied at least once a day during a treatment period of at least 4 weeks, 8 weeks, or 12 weeks. In one embodiment the cosmetic composition is applied twice a day during a treatment period of at least 4 weeks, 8 weeks, or 12 weeks.

III. Examples

Table 5 sets forth non-limiting prophetic examples of cosmetic compositions comprising a vitamin $B_3$ compound and a ricinoleate compound. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth.

TABLE 5

| Component | % by wt. | | | | |
|---|---|---|---|---|---|
| | Example 1 | Example 2 | Example 3 | Example 4 | Example 5 |
| Vitamin $B_3$ compound | 1 | 2 | 3 | 5 | 10 |
| Ricinoleate compound | 2 | 0.66 | 0.2 | 3.5 | 0.1 |
| Triethanolamine | QS to adjust pH 6 | QS to adjust pH 6 | QS to adjust pH 6 | QS to adjust pH 6 | QS to adjust pH 6 |
| Glycerin | 20 | 20 | 20 | 20 | 20 |
| Disodium EDTA | 0.1 | 0.1 | 0.1 | 0.1 | 0.1 |
| Tocopheryl Acetate | 0.1 | 0.1 | 0.1 | 0.1 | 0.1 |
| Isopropyl Lauroyl Sarcosinate | 2 | 2 | 2 | 2 | 2 |
| Isopropyl Isostearate | 1 | 1 | 1 | 1 | 1 |
| Sucrose Polycottonseedate | 0.5 | 0.5 | 0.5 | 0.5 | 0.5 |
| Polyemthylsilsesquioxane | 0.1 | 0.1 | 0.1 | 0.1 | 0.1 |
| Cetearyl Glucoside, Cetearyl Alcohol | 0.5 | 0.5 | 0.5 | 0.5 | 0.5 |
| Behenyl Alcohol | 0.5 | 0.5 | 0.5 | 0.5 | 0.5 |

TABLE 5-continued

| Component | % by wt. | | | | |
|---|---|---|---|---|---|
| | Example 1 | Example 2 | Example 3 | Example 4 | Example 5 |
| Ethylparaben | 0.2 | 0.2 | 0.2 | 0.2 | 0.2 |
| Propylparaben | 0.1 | 0.1 | 0.1 | 0.1 | 0.1 |
| Cetyl Alcohol | 0.25 | 0.25 | 0.25 | 0.25 | 0.25 |
| Stearyl Alcohol | 0.4 | 0.4 | 0.4 | 0.4 | 0.4 |
| PEG-100 Stearate | 0.2 | 0.2 | 0.2 | 0.2 | 0.2 |
| Polyacrylamide (and) C13-14 Isoparaffine (and) Laureth-7 | 2 | 2 | 2 | 2 | 2 |
| Panethnol | 1 | 1 | 1 | 1 | 1 |
| Benzyl Alcohol | 0.25 | 0.25 | 0.25 | 0.25 | 0.25 |
| Dimethicone and Dimethiconol | 1 | 1 | 1 | 1 | 1 |
| Water | QS | QS | QS | QS | QS |
| TOTAL | 100.00 | 100.00 | 100.00 | 100.00 | 100.00 |

The compositions herein may be prepared by conventional methods such as are known in the art of making topical compositions. Such methods typically involve mixing of the ingredients in one or more steps to a relatively uniform state, with or without heating, cooling, application of vacuum, and the like. Typically, emulsions are prepared by first mixing the aqueous phase materials separately from the fatty phase materials and then combining the two phases as appropriate to yield the desired continuous phase. The compositions may be prepared to optimize stability (physical stability, chemical stability, photostability) and/or delivery of the active materials. This optimization may include appropriate pH (e.g., less than 7), exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging), etc.

The dimensions and values disclosed herein are not to be understood as being strictly limited to the exact numerical values recited. In particular, U.S. Provisional Application Ser. No. 61/895,271 is incorporated herein by reference in its entirety. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cosmetic composition for topical application to skin, comprising:
    a synergistic combination of niacinamide and a ricinoleate compound selected from the group consisting of glyceryl ricinoleate, sodium ricinoleate, butyl acetyl ricinoleate, and methyl ricinoleate, wherein the synergistic combination has net observed luminescence counts that are more than 1.3 times greater than net calculated luminescence counts according to the Proteasomal Protease Assay; and
    a dermatologically acceptable carrier.

2. The cosmetic composition according to claim 1, wherein the vitamin B3 compound is selected from the group consisting of niacinamide, nicotinic acid, methyl nicotinate, and nicotinamide ribose and wherein the vitamin B3 compound has a concentration from about 1% to about 10% by weight of the cosmetic composition.

3. The cosmetic composition according to claim 1, wherein the ricinoleate compound has a concentration from about 1% to about 10% by weight of the cosmetic composition.

4. The cosmetic composition according to claim 1, wherein the dermatologically acceptable carrier is in the form of an emulsion.

5. The cosmetic composition according to claim 1, wherein the vitamin B3 compound is a derivative of niacinamide.

6. A method for treating a facial skin surface, comprising:
    identifying a target facial skin surface where skin lightening is desired; and
    applying a cosmetic composition to the target facial skin surface, wherein the cosmetic composition comprises a synergistic combination of niacinamide a ricinoleate compound selected from the group consisting of glyceryl ricinoleate, sodium ricinoleate, butyl acetyl ricinoleate, and methyl ricinoleate, and the synergistic combination has net observed luminescence counts that are more than 1.3 times greater than net calculated luminescence counts according to the Proteasomal Protease Assay; and a dermatologically acceptable carrier.

7. The method according to claim 6, wherein the vitamin B3 compound is selected from the group consisting of niacinamide, nicotinic acid, methyl niconate, and nicotinamide ribose and wherein the vitamin B3 compound has a concentration from about 1% to about 10% by weight of the cosmetic composition.

8. The method according to claim 6, wherein the ricinoleate compound has a concentration from about 1% to about 10% by weight of the cosmetic composition.

9. The method according to claim 6, wherein the cosmetic composition is applied to the facial skin surface for a period of time sufficient to up-regulate proteasomal chymotryptic protease activity.

* * * * *